(12) United States Patent
Zhang (10) Patent No.: US 6,278,024 B1
(45) Date of Patent: *Aug. 21, 2001

(54) ASYMMETRIC SYNTHESIS CATALYZED BY TRANSITION METAL COMPLEXES WITH RIGID CHIRAL LIGANDS

(75) Inventor: Xumu Zhang, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/524,787

(22) Filed: Mar. 13, 2000

Related U.S. Application Data (60) Division of application No. 09/190,155, filed on Nov. 12, 1998, which is a continuation-in-part of application No. 08/876,120, filed on Jun. 13, 1997, now Pat. No. 6,037,500.
(60) Provisional application No. 60/065,577, filed on Nov. 12, 1997, provisional application No. 60/085,786, filed on May 18, 1998, and provisional application No. 60/090,164, filed on Jun. 22, 1998.

(51) Int. Cl.$^7$ ....................................................... C07F 9/50
(52) U.S. Cl. ................................................. 568/17; 568/8
(58) Field of Search .......................... 568/8, 17; 558/155, 558/156

(56) References Cited

U.S. PATENT DOCUMENTS

| | | |
|---|---|---|
| 3,105,096 | 9/1963 | Welcher et al. . |
| 3,400,163 | 9/1968 | Mason et al. . |
| 5,008,457 | 4/1991 | Burk . |
| 5,171,892 | 12/1992 | Burk . |
| 5,177,230 | 1/1993 | Burk . |
| 5,258,553 | 11/1993 | Burk . |
| 5,426,223 | 6/1995 | Burk . |
| 5,491,266 | 2/1996 | Babin et al. . |
| 5,510,503 * | 4/1996 | Laue et al. .............................. 556/21 |
| 5,516,944 * | 5/1996 | Broger et al. .......................... 568/13 |
| 5,596,114 | 1/1997 | Burk . |

FOREIGN PATENT DOCUMENTS

| | | |
|---|---|---|
| WO 95/05354 | 2/1995 | (WO) . |
| WO 95/06025 | 3/1995 | (WO) . |
| WO 97/13763 | 4/1997 | (WO) . |

OTHER PUBLICATIONS

Sutton, B.M., et al., "An Alternate Synthesis, X–Ray Crystal Structure and P388 Activity of 1,2–Bis(dibenzophospholyl–1)ethane [1]. A Conformationally Constrained Analog of the Metal Ligand: 1,2–Bis-(diphenylphosphino)ethane," J. Heterocyclic Chem., vol. 27, No. 4, pp. 1123–1126 (1990).
Halterman, R.L., et al., "A Designed, Enantiomerically Pure, Fused Cyclopentadienyl Ligand with $C_2$ Symmetry: Synthesis and Use in Enantioselective Titanocene–Catalyzed Hydrogenation of Alkenes," J. Am. Chem. Soc., vol. 109, pp. 8105–8107 (1987).
Fryzuk, M.D., et al., "Asymmetric Synthesis. Production of Optically Active Amino Acids by Catalytic Hydrogenation," J. Am. Chem. Soc., vol. 99, No. 19, pp. 6262–6267 (1977).
Kagan, H.B., et al., "Asymmetric Catalytic Reduction with Transition Metal Complexes,"J. Am. Chem. Soc., vol. 94, No. 18, pp. 6429–6433 (1972).
Achiwa, K.J., "Asymmetric Hydrogenation with New Chiral Functionalized Bisphosphine–Rhodium Complexes," J. Am. Chem. Soc., vol. 98, No. 25, pp. 8265–8266 (1976).
MacNeil, P.A., et al., "Asymmetric Synthesis. Asymmetric Catalytic Hydrogenation Using Chiral Chelating Six–Membered Ring Diphosphines," J. Am. Chem. Soc., vol. 103, pp. 2273–2280 (1981).
Takaya, H., et al., "Synthesis of 2,2'–bis(diphenylphosphino)–1,1'–binaphtyl (BINAP), and Atropisomeric Chiral Bis(triaryl)phosphine, and Its Use in the Rhodium(I)–Catalyzed Asymmetric Hydrogenation of α–(Acylamino)acrylic Acids," J. Am. Chem. Soc., vol. 102, pp. 7932–7934 (1980).
Corey, E.J., et al., "New reagants for the Intermolecular and Intramolecular Pinacolic Coupling of Ketones and Aldehydes," J. Org. Chem., vol. 41, No. 2, pp. 260–265 (1976).
Greidinger, D.S., et al., "Alicyclic Studies," J. Org. Chem., vol. 22, pp. 1406–1410 (1957).
Brown, H.C., et al., "Hydroboration," J. Org. Chem., vol. 47, pp. 5074–5083 (1982).
Takaya, H., et al., "Practical Synthesis of (R)–or (S)–2, 2'–Bis(diarylphosphino)–1,1'–binaphthyls (BINAPS)," J. Org. Chem., vol. 51, pp. 629–635 (1986).
Miyashita, A., et al., "2,2'–Bis(diphenylphosphino)–1,1'–binaphthyl (BINAP). A New Atropisomeric Bis(triaryl)phosphine," tetrahedron, vol. 40, No. 8, pp. 1245–1253 (1984).
Burk, M.J., "$C_2$–Symmetric Bis(phospholanes) and Their Use in Highly Enantioselective Hydrogenation Reactions," J. Am. Chem. Soc., vol. 113, pp. 8518–8519 (1991).
Vineyard, B.D., et al., "Asymmetric Hydrogenation. Rhodium Chiral Bisphosphine Catalyst," J. Am. Chem. Soc., vol. 99, No. 18, pp. 5946–5952 (1977).
Ojima, I., et al., "N–carbamyl–4– diphenylphosphino–2–diphenylphospino-methylpyrrolidines (CAPP). Efficient New Chiral Ligands for Aymmetric Hydrogenation," Tetrahedron Letters, vol. 21, pp. 1051–1054 (1980).
Burk, M.J., et al., "New Electron–Rich Chiral Phosphines for Asymmetric Catalysis," Organometallics, vol. 9, pp. 2653–2655 (1990).
Nagel, U., et al., "Synthese N–substituierter (R,R)–3,4–Bis-(dyphenylphosphino) . . . ," Chem. Ber., vol. 119, pp. 3326–3343 (1986).

(List continued on next page.)

Primary Examiner—Jean F. Vollano
(74) Attorney, Agent, or Firm—Finnegan, Henderson, Farabow, Garrett & Dunner, L.L.P.

(57) ABSTRACT

This invention is to develop novel transition metal catalysts for the practical synthesis of important chiral molecules. The invention emphasizes asymmetric catalysis based on chiral bidentate phosphine ligands with cyclic ring structures which could be used to restrict conformational flexibility of the ligands and thus the efficiency of chiral transfer can be enhanced through the ligand rigidity

8 Claims, 3 Drawing Sheets

OTHER PUBLICATIONS

Knowles, W.S., et al., "Catalytic Asymmetric Hydrogenation," J.C.S., Chem. Comm., pp. 10–11 (1972).

Chen, Z., et al., "Asymmetric Synthesis and Metalation of $C_2$–Symmetric Annulated Bicyclooctylcyclopentadienes," Organometallics, vol. 10, pp. 3449–3458 (1991).

Trost, B.M., et al., "Asymmetric Transition Metal–Catalyzed Allylic Alkylations," Chem. Rev., vol. 96, pp. 395–422 (1966).

Consiglio, G., et al., "Enantioselective Homogeneous Catalysis Involving Transition–Metal–Allyl Intermediates," Chem. Rev., vol. 89, pp. 257–276 (1989).

Brunner, H., "Enantioselective Synthesis with Opticaly Active Transition–Metal Catalysts," Synthesis, pp. 645–654 (Sep. 1988).

Minami, T., et al., "The First Synthesis of Chiral Phosphinocarboxylic Acid Ligands, Trans–2–(dyphenyphosphino)cycloalkanecarboxylic Acids. The Phosphine–Palladium Complexes Catalyzed Asymmetric Allylic Alkylation," Tetrahedron Letters, vol. 31, No. 27, pp. 3905–3908 (1990).

Chen, Z., et al., "Syntheses of Novel Chiral Monophosphines, 2,5–Dialkyl–7–phenyl–7–phosphabicyclo–[2.2.1]heptanes, and Their Application in Highly Enantioselective Pd–Catalyzed Allylic Alkylations," J. org. Chem., vol. 62, pp. 4521–4523 (1997).

Hamada, Y. et al., "New Monodentate Chiral Phosphine 2,6–Dimethyl–9–phenyl–9–phosphabicyclo[3.3.1]nonane(9–PBN)," Tetrahedron Letters, vol. 37, No. 42, pp. 7565–7568 (1996).

Takaya, H., et al., "Asymmetric Hydrogenation," Catalytic Asymmetric Synthesis, Chapter 1, pp. 1–39 (1993).

* Burk, M.J., et al., "Preparation and Uses of $C_2$–Symmetric Bis(phospholanes): Production of α–Amino Acid Derivatives via Highly Enantioselective Hydrogenation Reactions," J. Am. Chem. Soc., vol. 115, pp. 10125–10138 (1983).

* Zhang, X., et al., "Asymmetric Hydrogenation of Cycloalkanones Catalyzed by BINAP–Ir(I)–Aminophosphine Systems," J. Am. Chem. Soc., vol. 115, pp. 3318–3319 (1993).

* Zhu, G., et al., "Highly Enanthioselective Rh–Catalyzed Hydrogenations with a New Chiral 1,4–Bisphosphine Containing a Cyclic Backbone," J. Am. Chem. Soc., vol. 119, No. 7, pp. 1799–1800 (1997).

* Arco, M.J., et al., "Synthesis of (±)–Nonactic Acid," J. Org. Chem., vol. 41, No. 12, pp. 2075–2083 (1976).

* Hughes, L., "The Mitsunobu Reaction," Organic Reactions, vol. 42, pp. 387–388 (1992).

* cited by examiner

FIG. 4 ASYMMETRIC HYDROGENATION OF SIMPLE KETONES CATALYZED BY Rh-Me-PennPhos COMPLEXES[a]

$$R \underset{R'}{\overset{O}{\|}} + H_2 \text{ (30 atm)} \xrightarrow[\text{2,6-Lutidine, MeOH}]{(\text{Rh(COD)Cl})_2 \text{ (0.5mol\%)} = 1} R \underset{R'}{\overset{OH}{\|}} (S)$$

| ENTRY | KETONE | EQUIV. OF LUTIDINE | EQUIV. OF KBr | TIME (H) | YIELD (?) | % ee | ENTRY | KETONE | EQUIV. OF LUTIDINE | EQUIV. OF KBr | TIME (H) | YIELD (?) | % ee |
|---|---|---|---|---|---|---|---|---|---|---|---|---|---|
| 1 | PhCOMe | 0.4 | — | 24 | 97 | 95 | 12 | iPrCOPh | 0.8 | 1.0 | 94 | 20 | 72 |
| 2 | | 0.4 | — | 53 | 94 | 95 | 13 | | 0.4 | — | 47 | 96 | 93 |
| 3 | | 0.4 | — | 53 | 97 | 94 | 14 | | 0.8 | 1.0 | 78 | 98 | 92 |
| 4 | | 0.4 | — | 72 | 34 | 60 | 15 | | 0.8 | 1.0 | 100 | 99 | 96 |
| 5 | | 0.8 | 1.0 | 102 | 77 | 86 | 16 | | 0.8 | 1.0 | 56 | 99 | 75 |
| 6 | | 0.8 | — | 108 | 56 | 91 | 17 | | 0.8 | 1.0 | 48 | 96 | 75 |
| 7 | H3CO | 0.8 | 1.0 | 48 | 83 | 94 | 18 | | 0.8 | 1.0 | 75 | 66 | 86 |
| 8 | H3CO | 0.8 | 1.0 | 106 | 99 | 95 | 19 | | 0.8 | 1.0 | 96 | 51 | 92 |
| 9 | OCH3 | 0.8 | 1.0 | 106 | 99 | 94 | 20 | | 0.8 | 1.0 | 94 | 99 | 84 |
| 10 | | 0.8 | — | 108 | 71 | 89 | 21 | | 0.8 | 1.0 | 106 | 90 | 92 |
| 11 | | 0.8 | 1.0 | 88 | 95 | 93 | | | | | | | | a. The reaction was carried out at rt under 30 atm of $H_2$ (substrate(0.5mmol,0.125M): (Rh(COD)Cl)$_2$: ligand (1) = 1:0.005:0.01). Conversion and % ee were determined by GC with a Supleco β-DEX 120 column. The absolute configuration (S) was determined by comparing the optical rotation with the reported value.[3-8]

ASYMMETRIC SYNTHESIS CATALYZED BY TRANSITION METAL COMPLEXES WITH RIGID CHIRAL LIGANDS

CROSS REFERENCE TO RELATED APPLICATIONS

This is a division of application Ser. No. 09/190,155, filed Nov. 12, 1998, which is a Continuation-In-Part of application Ser. No. 08/876,120, filed Jun. 13, 1997, now U.S. Pat. No. 6,037,500, and claims the benefit of U.S. provisional application nos. 60/065,577, filed Nov. 12 1997; 60/085.786, filed May 18, 1998: and 60/090,164, filed Jun. 22, 1998, all of which are incorporated herein by reference.

BACKGROUND OF THE INVENTION

Molecular chirality plays an important role in science and technology. The biological activities of many pharmaceuticals, fragrances, food additives and agrochemicals are often associated with their absolute molecular configuration. While one enantiomer gives a desired biological function through interactions with natural binding sites, another enantiomer usually does not have the same function and sometimes has deleterious side effects.

A growing demand in pharmaceutical industries is to market a chiral drug in enantiomerically pure form. To meet this fascinating challenge, chemists have explored many approaches for acquiring enantiomerically pure compounds ranging from optical resolution and structural modification of naturally occurring chiral substances to asymmetric catalysis using synthetic chiral catalysts and enzymes. Among these methods, asymmetric catalysis is perhaps the most efficient because a small amount of a chiral catalyst can be used to produce a large quantity of a chiral target molecule. During the last several decades, great attention has been devoted to discovering new asymmetric catalysts and more than a half-dozen commercial industrial processes have used asymmetric catalysis as the key step in the production of enantiomerically pure compounds. The worldwide sales of chiral drugs in 1997 was nearly $90 billion.

Figure 1:
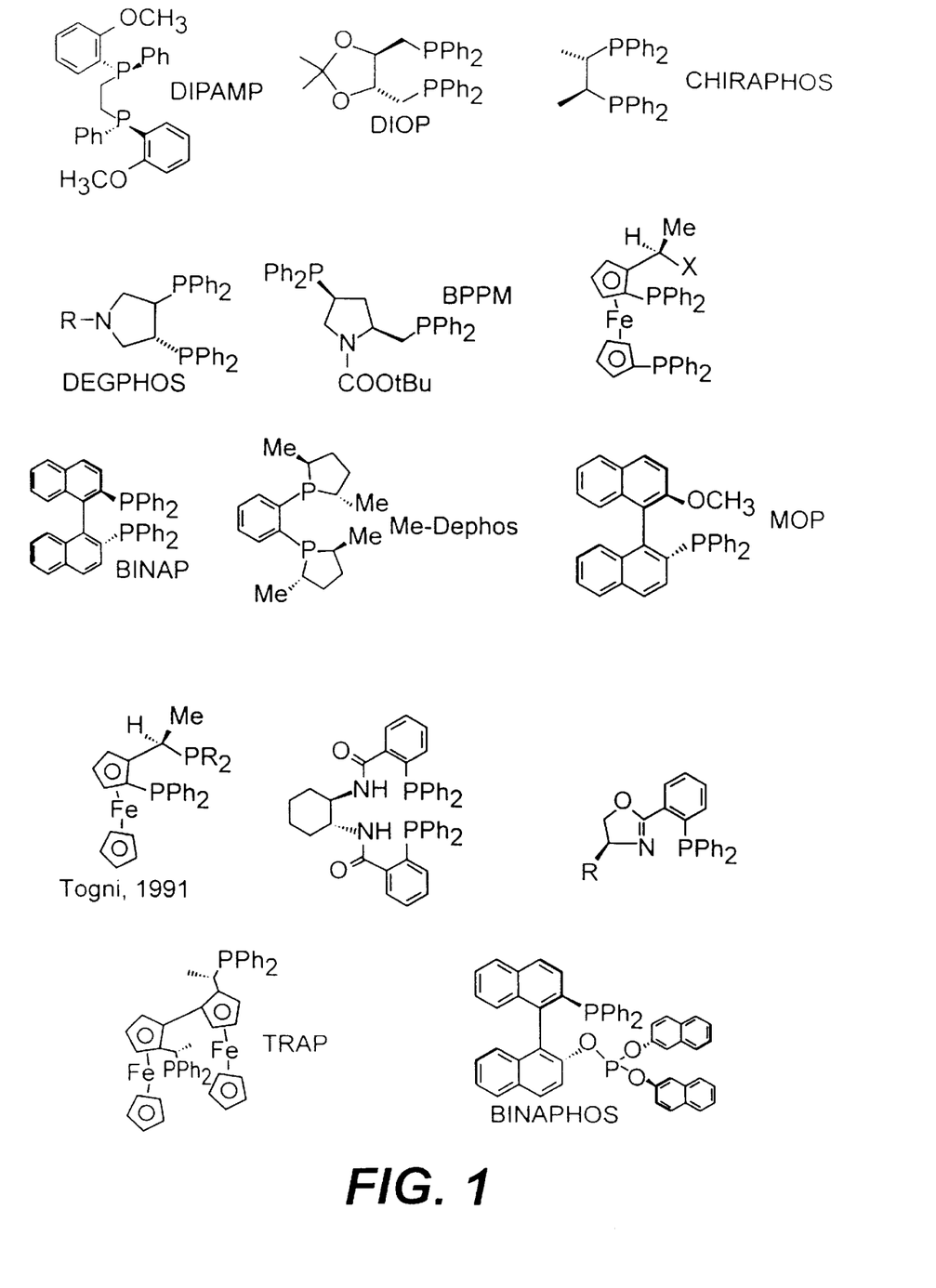
FIG. 1 shows prior art chiral ligands.

Many chiral phosphines (as shown in FIG. 1) have been made to facilitate asymmetric reactions. Among these ligands, BINAP is one of the most frequently used bidentate chiral phosphines. The axially dissymmetric, fully aromatic BINAP ligand has been demonstrated to be effective for many asymmetric reactions DUPHOS and related ligands have also shown impressive enantioselectivities in numerous reactions. However, there are many disadvantages associated with these ligands which hinder their applications.

These phosphines are difficult to make and some of them are air sensitive For DIPAMP, the phosphine chiral center is difficult to make. This ligand is only useful for limited application in assymmetric hydrogenation. For BPPM, DIOP, and Skewphos, the methylene group in the ligands causes conformational flexibility and enantioselectivities are moderate for many catalytic asymmetric reactions. DEG-PHOS and CHIRAPHOS coordinate transition metals in five-membered rings The chiral environment created by the phenyl groups is not close to the substrates and enantioselectivities are moderate for many reactions. BINAP, DuPhos, and BPE ligands are good for many asymmetric reactions. However, the rotation of the aryl-aryl bond makes BINAP very flexible. The flexibility is an inherent limitation in the use of a phosphine ligand. Furthermore, because the phosphine of BINAP contains three adjacent aryl groups, it is less electron donating than a phosphine that has less aryl groups. This is an important factor which influences reaction rates. For hydrogenation reactions, electron donating phosphines are more active. For the more electron donating DUPHOS and PBE ligands, the five-membered ring adjacent to the phosphines is flexible.

In co-pending application Ser. No. 08/876,120, the inventors herein disclosed, inter alia, the (2,2')-bis (diorganophosphino)-(1,1')bis(cyclic) family of chiral ligands, the (2,2')-bis(diorganophosphinoxy)-(1,1')-bis (cyclic) family of chiral ligands, and the family of chiral ligands comprising a rigid, fused phosphabicyclo[2.2.1] heptane structure named PennPhos, after Penn State University where the ligand was created. The common feature of these ligands is that they contain rigid ring structures which restrict conformational flexibility and promote efficient chiral transfer from the rigid ligand to desired products.

SUMMARY OF THE INVENTION

An object of the invention is to provide new chiral ligands.

A further object of the invention is to provide a detailed synthetic plan for making chiral ligands.

A further object of the invention is to provide methods of carrying out asymmetric synthesis using the chiral phosphine ligands of the present invention.

A further object of the invention is to provide methods for the efficient asymmetric synthesis of alcohols by enantioselective hydrogenation of ketones catalyzed by the chiral ligands of the invention.

A further object of the invention is to provide methods of using selected additives to improve the yield and enantioselectivity of selected asymmetric reactions.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention comprises a chiral bisphosphinite ligand having restricted conformational flexibility, wherein said ligand comprises an enantiomer of a substituted or unsubstituted (2, 2')-bis(diarylphosphinoxy)-(1,1')-dicyclo compound having saturated carbons at the 2, 2', 1, and 1' positions.

Exemplary embodiments of said ligand include (2S, 2'S)-bis(diphenylphosphinoxy)-(1R, 1 R')-dicyclopentane and (2R, 2'R)-bis(diphenylphosphinoxy)-(1R, 1 R')-dicyclopentane. These ligands are sometimes referred to herein as (S, S') BICPO, and (R, R') BICPO, respectively, or simply as BICPO.

The invention also comprises a chiral bisphosphine ligand for performing asymmetric synthesis, wherein said ligand is an enantiomer of a (2, 2')-bis(diarylphosphino)-(1,1')-dicyclo compound having saturated carbons at the 2, 2', 1, and 1' positions. In certain preferred embodiments, the ligand comprises an enantiomer of a (2, 2')-bis (diarylphosphino)-(1,1')-dicyclo compound having saturated carbons at the 2, 2', 1, and 1' positions, and each aryl is 3, 5-alkyl substituted or 4-alkyl substituted. These ligands are sometimes referred to herein as modified BICP.

The invention comprises various methods for performing chiral synthesis using catalysts comprising the ligands disclosed in this application, and in the parent Application Serial No. 081876,120, including methods for synthesis of a chiral product in an enantiomeric excess from an organic substrate, comprising metal catalyzed asymmetric hydrogenation, wherein said asymmetric hydrogenation comprises the step of reacting an organic substrate in the presence of a catalyst, wherein the catalyst comprises a transition metal and a chiral ligand, and said chiral ligand comprises a phosphabicyclo[2.2.1] heptyl compound It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DETAILED DESCRIPTION OF THE INVENTION

The ligands of the present invention are generally used with transition metals. Specifically, transition metals known to be useful in organic synthesis are used. Examples of the transition metals used are the group VIII metals, such as rhodium, iridium, ruthenium, and nickel. More preferably, transition metal catalyst precursors are used in conjunction with the ligands to make a catalyst suitable for asymmetric synthesis. Suitable transition metal catalyst precursors include, but are not limited to, [Rh(COD)Cl]$_2$, [Rh(COD)$_2$]X, or [Ir(COD)Cl]$_2$, [Ir(COD)$_2$]X, or Ni(ally)X wherein X is BF$_4$, ClO$_4$, SbF$_6$, CF$_3$SO$_3$, or equivalents, and COD is cyclooctadiene. The catalysts can be, for example, Ru(RCOO)$_2$(diphosphine), RuX'2(diphosphine), where X' is chlorine or bromine. Other group VIII catalysts with chiral phosphines besides those mentioned above are known to those of skill in the art.

As used herein, enantiomeric excess refers to the excess of one enantiomer over another in the reaction product.

$$\% \text{ enantiomeric excess} = \frac{[R] - [S]}{[R] + [S]} \times 100$$

In general, the catalyst systems of the present invention produce chiral products with higher enantiomeric excess than in the prior art. In some instances, depending on the reaction involved, enantiomeric excess was found to be greater than about 70%. In still other cases, the enantiomeric excess of the product was greater than about 80%. The enantiomeric excess of still other reaction products has been found to be greater than about 90%, even approaching 100% enantiomeric excess in the case of some reactions disclosed herein.

BICP and BICPO

The BICP and BICPO ligands can be synthesized as set forth in co-pending application 08/876,120, with variations set forth below and with other variations as would be obvious to one of ordinary skill in the art.

One example of BICP is shown below in scheme (I). The scheme (I) below is exemplary only. The cycles of the bis(cyclic) structure may comprise alkyl and aryl substituents and may further contain fused substituents.

(I)

The synthesis of BICP is set forth under Section VI, "Experimental" below.

A modified variation of the BICP ligand comprises substituents on the diarylphosphino structure. In one embodiment, the aryl substituent is 3,5-alkyl substituted or 4-alkyl substituted, as shown above in scheme I. In a preferred embodiment, the diarylphosphino structures are 3,5-dimethyl substituted, although other structures are possible, as would be apparent to one of ordinary skill in the art.

Figure 3:
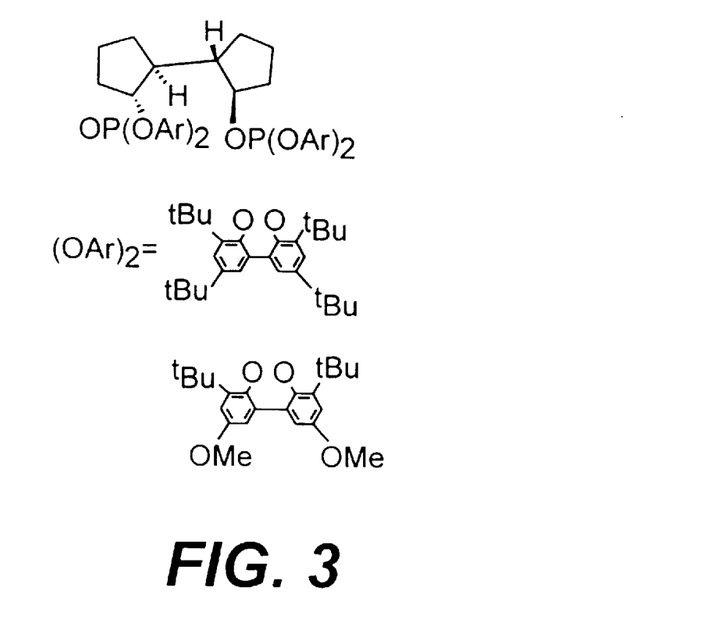
FIG. 3 shows the BICPO ligand with contemplated phosphine groups.

The chiral bisphosphinite ligand family (2S, 2'S)-bis(diarylphosphinoxy)-(1R, 1'R)-dicyclo compounds, and more particularly (2S, 2'S)-bis(diphenylphosphinoxy)-(1R, 1'R)dicyclopentane) (sometimes hereinafter referred to as "(1R, 1'R, 2S, 2'S)-BICPO" or simply "BICPO") is easily made from chiral (1R,1'R)-bicyclopentyl-(2S, 2'S)-diol in high yield as illustrated below (scheme II):

In an advantageous modification, the BICPO ligand comprises diarylphosphine groups or diaryloxy phosphine groups in place of the diphenylphosphine groups shown above. As shown in Scheme 3, the ligand may comprise a biphenyl group having oxygens bonded at the 2 and 6' positions, wherein a phosphorus in each diarylphosphinoxy group is bonded to said oxygens, and wherein the 3, 5, 3', and 5' positions of said biphenyl group are substituted with alkyl or alkoxy substituents. In a preferred embodiment, the 3, 5, 3' and 5' positions are substituted with methyl, tert-butyl or methoxy substituents. Biphenyl substituents with oxygens at the 2 and 6' positions are known per se from U.S. Pat. No. 5,491,266, incorporated by reference herein.

Highly Enantioselective Rhodium-Catalyzed Hydrogenation of Dehydroamino Acids with Chiral Bisphosphinites In contrast to many chiral phosphines reported in the literature, phosphinites used in metal complexes for asymmetric reactions are generally rather poor ligands. However, although phosphinites are less electron donating than phosphines, they can be excellent ligands for asymmetric hydroformylation and hydrocyanation reactions. Clearly, it is worthwhile to search for new chiral phosphinites for asymmetric catalysis. Taking advantage of the relatively rigid bis-cyclopentane backbone of BICP, we made the corresponding chiral bisphosphinite, (2S, 2'S)-bis(diphenylphosphinoxy)-(1R, 1'R)-dicyclopentane (abbreviated (1R, 1'R, 2S, 2'S)-BICPO). We have also synthesized (2R, 2'R)-bis(diphenylphosphinoxy)-(1R, 1'R) dicyclopentane (abbreviated (1R, 1'R, 2R, 2'R)-BICPO. Rhodium complexes of these ligands are excellent catalysts for asymmetric hydrogenation of α-(acylamino)acrylic acids, giving up to 96% enantiomeric excess. These phosphinite ligands contain two cyclopentane rings which restrict their conformational flexibility, and high enantioselectivity in asymmetric hydrogenation can be achieved despite the formation of a nine-membered ring metal-ligand complex.

The cationic Rh(I)-complex [Rh(COD)(BICPO)]BF$_4$, prepared in situ by mixing [Rh(COD)$_2$]BF$_4$ with 1.1 molar equivalents of (1R, 1'R, 2S, 2'S)-BICPO under an inert atmosphere, is a highly effective catalyst for the hydrogenation of α-acetoamidocinnamic acid at ambient temperature under 1 atmosphere of H$_2$. Scheme III below was carried out at room temperature under 1 atm of hydrogen for 24 hours.

(II)

The ratio of substrate (0.5 mmol. 0.125 M):[Rh(COD)$_2$] BF$_4$:ligand(1R, 1'R, 2S, 2'S BICPO) was equal to 1:0.01:0.011. The reaction mixture was treated with CH$_2$N$_2$, then concentrated in vacuo. The residue was passed through a short silica gel column to remove the catalyst. The enantiomeric excesses were measured by capillary GC or HPLC. The absolute configuration of products was determined by comparing the observed rotation with the reported value.

Table 1 summarizes the results of hydrogenation of α-acetoamidocinnamic acid under a variety of experimental conditions. The reaction medium significantly affects the catalyst activity and enantioselectivity of the product. Unlike our early observation on the additive effect of triethylamine with the BICP system, the enantioselectivity and reactivity of the hydrogenation decreased drastically in the presence of a catalytic amount of triethylamine (Rh:(1R, 1'R, 2S, 2'S)-BICPO]:Et$_3$N=1:1.1:50). For example, α-acetoamidocinnamic acid was completely reduced with 89.1% enantiomeric excess in MeOH in the absence of Et$_3$N while only 30% was reduced with 20.7% enantiomeric excess with a catalytic amount of Et$_3$N under 1 atmosphere of H$_2$ (entry 3 vs 2, entry 5 vs 4). Asymmetric hydrogenation in alcoholic solvents (entries 4, 6, and 8–9), except with CF$_3$CH$_2$OH (entry 7) gave better selectivities than in THF (entry 2) and ClCH$_2$CH$_2$Cl (entry 1) Among several common alcohol solvents, the highest enantioselectivity (94.7% enantiomeric excess, S) for the hydrogenation of α-acetoamidocinnamic acid was achieved in $^i$PrOH under 1 atm of H$_2$ at ambient temperature (entry 9). The best result (96.1% enantiomeric excess, 100% conversion) for the hydrogenation of α-acetoamidocinnamic acid was obtained when (1R, 1'R, 2S, 2'S)-BICPO was used in PrOH from 1 atmosphere of H$_2$ at 0° C. (entry 10). A neutral rhodium catalyst formed in situ from (1R, 1'R, 2S, 2'S) BICPO and [Rh(COD)Cl]$_2$ is less effective than the cationic [Rh(COD) $_2$]BF$_4$ described above (entry 11).

TABLE 1

Rh-Catalyzed Asymmetric Hydrogenation of α-Acetamidocinnamic Acid

| Entry | Solvent | Et$_3$N(%) | Con. (%) | ee(%) |
|---|---|---|---|---|
| 1 | ClCH$_2$CH$_2$Cl | — | 100 | 88.2 |
| 2 | THF | — | 100 | 89.1 |
| 3 | THF | 50 | 30 | 30.9 |
| 4 | MeOH | — | 100 | 92.4 |
| 5 | MeOH | 50 | 100 | 67.9 |
| 6 | EtOH | — | 100 | 92.0 |
| 7 | CF$_3$CH$_2$OH | — | 100 | 80.3 |
| 8 | $^t$BUOH | — | 100 | 91.1 |
| 9 | $^i$PrOH | — | 100 | 94.7 |
| 10$^c$ | $^i$PrOH | — | 100 | 96.1 |
| 11$^d$ | $^i$PrOH | — | 86.6 | 63.9 |

$^c$Reaction was carried out at 0° C.
$^d$[Rh(COD)Cl]$_2$ (0.5 mol %) was used as the catalyst precursor.

Percent conversion and percent enantiomeric excess were determined by GC using a Chirasil-VAL III FSOT column on the corresponding methyl ester. The S absolute configuration was determined by comparing the optical rotation with the value reported in Burk, M. J., et al., *J. Am. Chem. Soc.* 1993, 115, 10125, incorporated herein by reference.

The absolute configurations at the 2, 2'-positions are opposite in (1R, 1'R, 2R, 2'R) BICP and (1R, 1'R, 2S, 2'S) BICPO, but in the asymmetric hydrogenation of α-acetoamidocinnamic acid, both gave the same amino acid: S-N-acetylphenylalanine. These results suggest that these reactions, promoted by a seven membered (1R, 1'R, 2R, 2'R)-BICP-Rh complex and a nine membered (1R, 1'R, 2S, 2'S)-BICPO-Rh complex, may proceed via different pathways. It is apparent that there must be careful matching of the catalyst chiral environment to the substrate in order to obtain high selectivity.

Using (1R, 1'R, 2R, 2'R)-BICPO as the ligand under the conditions that gave the best results for hydrogenation with (1R, 1'R, 2S, 2'S)-BICPO, α-acetoamidocinnamic acid was reduced completely to give (R)-N-acetylphenylalanine as the product with slightly lower enantioselectivity (83.51% enantiomeric excess).

Several dehydroamino acids were hydrogenated with the Rh-(1R, 1'R, 2S, 2'S)-BICPO catalyst according to the following general reaction:

The results are tabulated below in Table 2. High selectivity was achieved for the hydrogenation of α-(acetoamido) acrylic acid (94.8% enantiomeric excess, entry 1 in Table 2). Over 90% enantiomeric excesses have been obtained for many substituted α-acetoamidocinnamic acids. The enantioselectivity for the hydrogenation of dehydro-N-acetylleucine was lower than for other substrates (entry 11 in Table 2). The overall enantioselectivities are comparable or slightly lower than the enantioselectivities attained previously with the best chiral bisphosphines or bisphosphinites, which form five to seven-membered ring complexes with transition metals. However, compared with the nine-membered chelated bidentate ligands reported in the prior art our new bisphosphinites (1R, 1'R, 2S, 2'S) BICPO and (1R, 1'R, 2R, 2'R) BICPO display the highest reactivities and enantioselectivities in the rhodium-catalyzed asymmetric hydrogenation of α-(acylamino)acrylic acids.

TABLE 2

Asymmetric Hydrogenations of Dehydroamino Acid Derivatives

| Entry | Substrate | % ee[a] |
|---|---|---|
| 1 | R = H, R' = CH$_3$ | 94.8 |
| 2 | R = Ph, R'= CH$_3$ | 94.7 |
| 3 | R = Ph, R' = Ph | 89.2 |
| 4 | R = m-Br-Ph, R' = CH$_3$ | 93.5 |
| 5 | R = o-Cl-Ph, R' = CH$_3$ | 92.9 |
| 6 | R = p-F-Ph, R' = CH$_3$ | 91.1 |
| 7 | R = p-MeO-Ph, R' = CH$_3$ | 93.2[b] |
| 8 | R = p-OAc-m-OMePh, R' = CH$_3$ | 95.0[b] |
| 9 | R = 2-naphthyl, R' = CH$_3$ | 91.4 |
| 10 | R = 2-thienyl, R' = CH$_3$ | 90.1 |
| 11 | R = i-Pr, R' = CH$_3$ | 45.7 |

[a]The S absolute configurations were determined by comparing optical rotation with reported values. The % enantiomeric excess was determined by GC using a Chirasil-VAL III FSOT column on the corresponding methyl ester.
[b]The % enantiomeric excess was determined by HPLC using a Chiralcel OJ column on the corresponding methyl esters.

The mechanism of asymmetric hydrogenation of dehydroamino acids has been examined intensively. It is generally accepted that a chiral ligand which can form a rigid ligand-metal complex is essential for effective chiral recognition. The presently disclosed new class of BICPO phosphinites, which form nine membered chelated complexes with rhodium, gave remarkably high selectivities for the hydrogenation of dehydroamino acids. The key element of this system is that the two cyclopentane rings in the backbone restrict the conformational flexibility of the nine-membered ring, and the four stereogenic carbon centers in the backbone dictate the orientation of four P-phenyl groups.

Additive Effects in the Rh-PennPhos Catalyzed Asymmetric Hydrogenation of Acetophenone New chiral bisphosphines based on the 1,2-bis{(2,5-endo-dialkyl-1-7-phosphabicyclo[2.2.1]heptyl} benzene skeleton (sometimes hereinafter abbreviated as "PennPhos") were synthesized. A rhodium complex with (R, S, R, S) Me-PennPhos is an excellent catalyst for asymmetric hydrogenation of acetophenone, giving up to 96% enantiomeric excess of the (S) alcohol. These ligands contain a conformationally rigid phosphabicyclo[2.2.1]heptane framework, which dictates the approach of ketone substrates and thus leads to high enantioselectivity in asymmetric reactions. Detailed studies reveal the presence of catalytic amounts of additives is important for achieving high conversion and enantioselectivity in the hydrogenation reaction. Compared with prior art Rh catalysts, this catalytic system gives higher enantioselectivity in acetophenone reduction.

We have designed conformationally rigid 2,5-endo-dialkyl-7 phosphabicyclo[2.2.1]heptanes as new chiral ligands and have demonstrated that these monophosphine species can be more effective for some asymmetric reactions than the conformationally flexible phosphacyclopentane. Herein we report the synthesis, and application of novel conformationally rigid chiral bisphosphines. 1,2-bis(2,5-endo-dialkyl-7-phosphabicyclo[2.2.1 ]heptyl)benzene (abbreviated as PennPhos).

Figure 2:
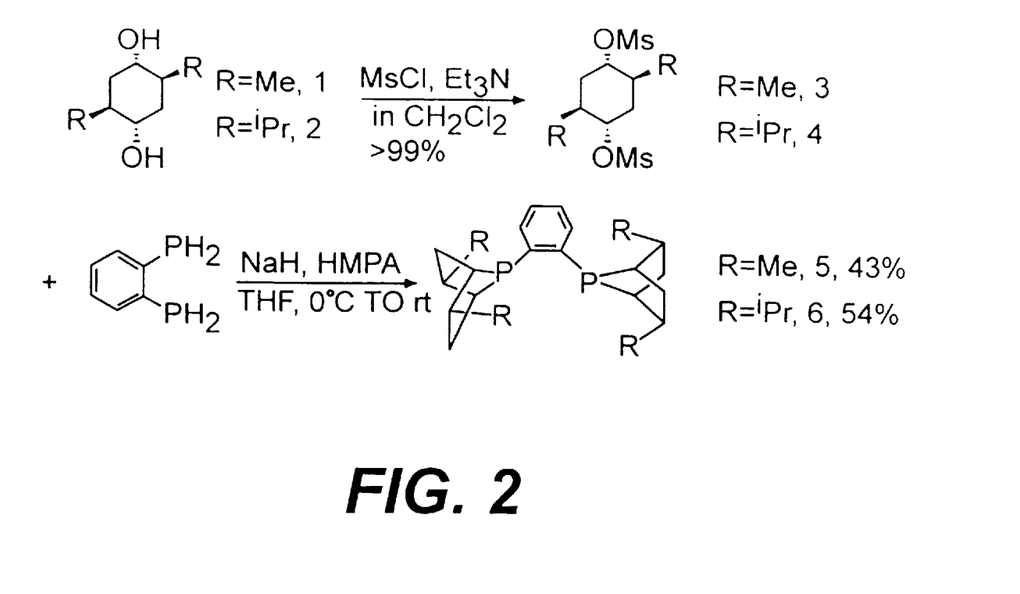
FIG. 2 shows a scheme for synthesis of the PennPhos Ligand.

The synthesis of PennPhos is illustrated in Scheme 2. These ligands are air-stable solids and can be handled easily on the bench top. These characteristics are in stark contrast to the DuPhos ligand, known to the prior art, which is conformationally flexible, a liquid at room temperature and unstable in air.

We have devoted much attention to enantioselective hydrogenation of simple ketones—one of the most fundamental reactions in organic chemistry—as a showcase for the development of new applications based on transition metal catalysts. Among the known group VIII transition metal complexes, the most effective catalyst for hydrogenation of simple aromatic ketones is the Ru-BINAP-chiral diamine-KOH system disclosed, for example, in X. Zhang, et al. J. Am. Chem. Soc., 1993, 115, 3318, which produced an enantiomeric excess on the order of 87–99%. Much lower enantioselectivities were reported with Rh and other metal catalysts bearing chiral bisphosphines. Development of a truly efficient catalytic system for enantioselective hydrogenation of simple ketones remains a challenging goal in synthetic chemistry. Since PennPhos ligands are more electron rich than triaryl phosphines, Rh-PennPhos catalysts have good activity towards asymmetric hydrogenation of simple ketones.

TABLE 3

| | | Equiv. of Additive vs Rh-Catalyst Conversion (% ee) | | | | | |
|---|---|---|---|---|---|---|---|
| Entry | Additive | 0.0 | 0.1 | 0.15 | 0.2 | 0.3 | 1.0 |
| 1 | NaOMe | 45(57) | 56(70) | 69(83) | 71(88) | 41(80) | 25(15 R) |
| 2 | NaOH | | 79(84) | | 85(91) | 43(86) | 23(25 R) |
| 3 | NaOPh | | | 67(77) | 80(87) | 54(28) | 16(28 R) |

TABLE 3-continued

| | | \multicolumn{6}{c}{Equiv. of Additive vs Rh-Catalyst Conversion (% ee)} | | | | | |
|---|---|---|---|---|---|---|---|
| Entry | Additive | 0.0 | 0.1 | 0.15 | 0.2 | 0.3 | 1.0 |
| 4 | LiOBu$^t$ | | | 80(91) | 58(89) | 19(78) | 20(23 R) |
| 5 | LiCl | | 49(66) | | 46(70) | 47(72) | 44(67) |
| 6 | KF | | 78(84) | | 87(91) | 73(90) | 39(87) |
| 7 | KBr | | 74(80) | | 82(88) | 85(89) | 89(92) |
| 8 | KI | | 71(81) | | 77(86) | 73(90) | 15(73) |
| 9 | Et3N | | | | 78(92) | 28(82) | 18(4 R) |
| 10 | DBU | | | | 81(90) | 39(84) | 18(26 R) |
| 11 | Proton Sponge | | | 75(86) | 84(90) | 31(81) | 10(21 R) |
| 12 | Pyridine | | 56(77) | | 47(74) | 33(70) | 13(55) |
| 13 | 2-Me-Imidazole | | 86(87) | | 94(94) | 79(92) | 12(1) |
| 14 | DABCO | | 78(87) | 84(90) | 88(95) | 55(92) | 9(63) |
| 15 | 2,6-Lutidine | | 72(83) | 84(90) | 94(94) | 97(95) | 93(95) |
| 16 | 2,4,6-Collidine | | 82(88) | 90(92) | 97(95) | 96(96) | 75(95) |

Table 3 outlines the asymmetric hydrogenation results using acetophenone as a typical substrate and a rhodium complex of 1,2-bis(2,5-endo-dimethyl-phosphabicyclo [2.2.1]heptyl) benzene (Me-PennPhos) as the catalyst according to the following:

The reaction was carried out at room temperature under 30 atm of H$_2$ for 24 hours. The ratio of substrate (0.5 mmol. 0.125 M):[Rh(COD)Cl]$_2$:ligand was 1:0.005:0.01. Conversion and percent enantiomeric excess were determined by GC with a Supleco β-DEX 120 column. The absolute configuration was determined by comparing the optical rotation of the product with values reported in the literature.

Initial extensive screening of catalytic conditions shows that the asymmetric hydrogenation gives good enantioselectivity and activity using [Rh(COD)Cl]$_2$ as the precursor under 30 atm of H$_2$ in MeOH. A significant finding in our study is the dramatic effect of additives in the catalytic system. Not only does the enantioselectivity strongly depend on the additives used, but catalytic activity also varies to a great extent.

Three major classes of additives have been screened in the catalytic system: ionic bases (entries 1–4), halide (entries 5–8) and neutral bases (entries 9–16).

The enantioselectivity of the reaction is a useful probe for understanding the reaction mechanism of the Rh-catalyzed hydrogenation. In the absence of additives, asymmetric hydrogenation of acetophenone catalyzed by the Rh-Me-PennPhos complex is sluggish and gives the secondary alcohol in only 57% enantiomeric excess (entry 1). In the presence of catalytic amounts of additives (0.1–0.2 equiv. vs. Rh), both reactivity and enantioselectivity are increased.

Depending on the additives and the amount of the additives introduced, different effects are observed. For the four ionic bases (entries 1–4), addition of 1 equiv. of base to Rh shuts off the reaction and surprisingly gives alcohol with the opposite enantioselectivity. The halide effect was studied using different salts (entries 5–8). The presence of excess chloride shows little effect on the catalyst activity and selectivity (entry 5). Addition of iodide or fluoride ion initially accelerates the reaction and gives higher enantioselectivity (0.1–0.3 equiv.). However, both enantioselectivity and activity drop when 1 equiv. of halide is used (entries 6 and 8). Interestingly, bromide can enhance both enantioselectivity and rate of the reaction over the entire concentration range (0.1 to 1 equiv., entry 7). Common organic amine bases (Et$_3$N (entry 9), DBU (entry 10), and proton spronge (entry 11)) were also examined as additives. Higher conversion and better enantioselectivity were observed when less than 0.2 equiv of base was present in the catalytic system. Using more than 0.3 equiv of the base causes a decrease in reactivity and enantioselectivity. The reaction gives the opposite enantioselectivity with low conversion when using 1 equiv. of the amine base (entries 9–11). 2-methyl-imidazole and DABCO (entries 12–14) also goes through first enhancement and then erosion of both the reactivity and selectivity. However, we found that 2,6-lutidine and 2,4,6- collidine have a different effect. Both enantioselectivity and conversion are increased when 0.1 to 1 molar equivalent of these bases are used in the catalytic system (entries 15–16). Up to 96% enantiomeric excess is observed for the hydrogenation of acetophenone, which is the highest enantioselectivity achieved with a group VIII transition metal hydrogenation catalyst. Thus, we have found that bromide ion, 2,6-lutidine and 2,4,6-collidine are useful promoters for the Rh-catalyzed enantioselective hydrozenation of acetophenone. Preferred concentrations of these additive range between 0.1 and 1.0 molar equivalents with respect to the transition metal used. Most preferred amounts of additive are 0.2 to 0.3 molar equivalents of the additives with respect to the transition metal.

Highly Enantioselective Hydrogenation of Simple Ketones Catalyzed by a Rh-PennPhos Complex (R, S, R, S) Me-PennPhos was used as an effective ligand for asymmetric hydrogenation of simple ketones. Up to 96% enantiomeric excess has been obtained in the hydrogenation of many alkyl aryl ketones catalyzed by the Me-PennPhos-Rh compound. Furthermore, enantiomeric excesses ranging from 73% to 94% were achieved with a variety of alkyl methyl ketones. The Me-PennPhos-Rh catalyst offers higher enantioselectivity than was available with the hydrogenation catalysts of the priorm art.

Asymmetric reduction of ketones to secondary alcohols is one of the most fundamental molecular transformations in organic chemistry. While efficient transition metal-catalyzed asymmetric hydrogenation systems for functionalized ketones have been realized, highly enantioselective hydrogenation with simple ketones that lack heteroatoms which can anchor the transition metals is not fully developed. Much effort have been focused on this active research area. Stoichiometric and catalytic hydride reduction, transfer hydrogenation, hydrosilylation and direct hydrogenation have been investigated extensively. Highly enantioselective reduction systems include boron reagents, alumina reagents, and oxazaborolidine catalysts. Although some of those systems have been widely used in academic labs and in industry, they are still far from a desirable "green" process in terms of reactivity because large amounts of waste are generated when using these stoichiomeric reducing agents or catalysts with low turnovers. Prompted by the high catalytic turnovers for the reduction of ketones based on transition metal catalysts, many groups have devoted their efforts to search new catalytic systems. Among the direction hydrogenation catalysts, promising results were achieved for asymmetric hydrogenation of aromatic ketones facilitated by a BINAP-Ru(II)-chiral diamine-KOH complex. In this complicated system, chiral diamine serve's as an important stereochemistry controlling element as chiral BINAP. So far, none of simple metal-chiral bisphosphine complexes can be used for highly enantioselective hydrogenation of simple ketones. Furthermore, reduction of simple alkyl ketones generally gives low enantioselectivity in all systems with a few exceptions. To develop an efficient hydrogenation catalyst for simple ketones, we have recently made a novel conformationally rigid chiral bisphosphine, 1,2-bis{(1R, 2S, 4R, 5S)2.5-endo-dimethyl-7phosphabicyclo[2.2.1]heptyl}benzene (abbreviated as (R. S. R, S) Me-PennPhos), as disclosed herein.

Searching proper conditions for asymmetric reactions often is tedious and challenging work. Extensive screening on catalytic conditions shows that the asymmetric hydrogenation gives good enantioselectivity and activity using [Rh (COD)Cl]$_2$ as the precursor under 30 atm of H$_2$ in MeOH. We have found that bromide and 2,6-lutidine are important promoters for the Rh-catalyzed enantioselective hydrogenation of simple ketones. The major function of 2,6-lutidine may be to deprotonate Rh—H while the conjugated acid or MeOH can hydrolyze the Rh—OR bond.

Figure 4:
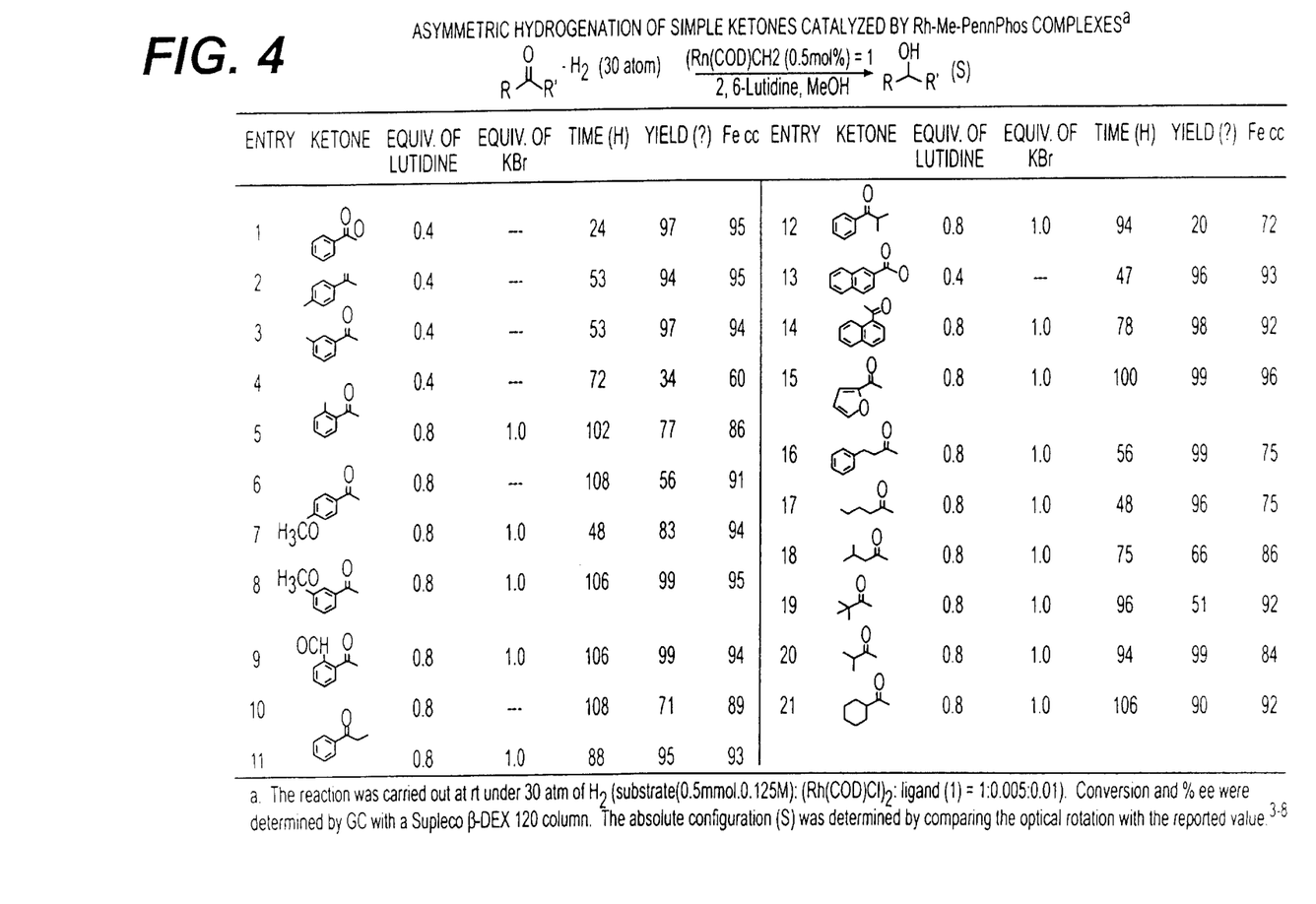
FIG. 4 summarizes the results of asymmetric hydrogenation of various simple ketones with Rh-Me-PennPhos complexes.

FIG. 4 summarizes the asymmetric hydrogenation results using various simple ketones as substrates and a Rh—I complex as the catalyst. Two sets of reaction conditions were applied to achieve high enantioselectivity: introduction of 0.4 equiv of 2,6-lutidine vs Rh or addition of both 0.8 equiv of 2,6-lutidine and 1 equiv of KBr vs Rh. For most aryl methyl ketones (entries 1–3, entries 6–9 and entries 13–15), constant high enantioselectivities (% enantiomeric excess ranging from 93 to 96) were observed. The reactivity and enantioselectivity drop with aryl methyl ketones which have an ortho substituted alkyl on the aryl group (entry 4). However, hydrogenation of potential chelating ketones (entry 9 and 15) gives high enantioselectivity. Presence of both 2,6-lutidine and KBr accelerates the enantioselectivy and activity (entry 5 vs 4; entry 7 vs 6; entry 11 vs 10). This condition was then used for the hydrogenation reaction of other ketone substrates. Increasing the bulk of the methyl group to ethyl or isopropryl in the alkyl aryl ketones dramatically decreases the activity and enantioselectivity (entry 1 vs entry 10, entry 11 vs entry 12). This clearly indicates that the chiral environment in Rh-1 can effectively discriminate methyl against other alkyl groups. To confirm this assumption, we have carried out asymmetric hydrogenation of several alkyl methyl ketones (entries 16–21). Up to 94% enantiomeric excess for t-butyl methyl ketone (entry 19) and 92% enantiomeric excess for cyclohexyl methyl ketone (entry 21) were obtained. The enantioselectivity decreases when the size of alkyl group becomes smaller. With isopropryl methyl ketone and isobutyl methyl ketone, 84% ee (entry 20) and 85% ee (entry 18) were achieved, respectively. However, even with unbranched alkyl groups in the alkyl methyl ketones, high enantioselectivities (73% ee, entry 16) and (75% ee, entry 17) are still achievable. To the best of our knowledge, asymmetric hydrogenation of alkyl methyl ketones catalyzed by Rh-PennPhos gives higher enantioselectivity compared with other hydrogenation catalysts.

In conclusion, we have developed the PennPhos system as a highly enantioselective hydrogenation catalyst for both alkyl aryl ketones and alkyl methyl ketones.

EXPERIMENTAL

In all of the syntheses described herein, unless otherwise indicated, all reactions were carried out under nitrogen. THF and ether were freshly distilled from sodium benzophenone ketyl. Toluene and 1,4-dioxane were freshly distilled from sodium. Dichloromethane and hexane were freshly distilled from CaH$_2$. Methanol was distilled from magnesium and CaH$_2$. Reactions were monitored by thin-layer chromatography (TLC) analysis. Column chromatography was performed using EM silica gel 60 (230–400 mesh). 1 H NMR were recorded on Bruker ACE 200, WP 200, AM 300 and WM 360 spectrometers. Chemical shifts are reported in ppm downfield from tetramethylsilane with the solvent resonance as the internal standard (CDCl$_3$, δ7.26 ppm). $^{13}$C, 31P and $^1$H NMR spectra were recorded on Bruker AM 300 and WM 360 or Varian 200 or 500 spectrometers with complete proton decoupling. Chemical shifts are reported in ppm downfield from tetramethylsilane with the solvent resonance as the internal standard (CDCl$_3$, δ77.0 ppm). Optical rotation was obtained on a Perkin-Elmer 241 polarimeter. MS spectra were recorded on a KRATOS mass spectrometer MS 9/50 for LR-EI and HR-EI. GC analysis were carried on Helweft-Packard 5890 gas chromatograph with a 30-m Supelco β-DEX™ column. HPLC analysis were carried on WatersTM 600 chromatograph with a 25-cm CHIRALCEL OD column.

Synthesis of BICP 1,1'-Dihydroxy-1,1'-dicyclopentyl (1) was synthesized from cyclopentanone as follows:

Mercuric chloride (20 g, 73 mmol) and benzene (300 ml) were added to a 2 L three-necked round bottom flask. Coarse aluminum powder (40 g, 1.48 mol) was added to this mixture at a rate sufficient to keep benzene at reflux. The mixture was stirred at room temperature for 15 min. Cyclopentanone (200 g, 2.4 mol) was added dropwise to the suspension of Al—Hg alloy in benzene (~8 h) and the mixture was stirred for an additional 2 hours. The reaction mixture was cooled at 0° C. and iced water (100 mL) was added. Diethyl ether (300 mL) was added to extract products. The mixture was filtered through a celite and the filtrate was washed with ether. The combined organic phase was dried over $Na_2SO_4$ and evaporated under vacuum. 1,1'-Dihydroxy-1,1'-dicyclopentyl (1) (120) was obtained as a white solid, yield 56%. 1,1'-dicyclopentyl (2) was synthesized from (1) as follows:

Pyridine (84 mL, dried over NaOH), $POCl_3$ (17 mL) and 1,1'-Dihydroxy- 1,1'-dicyclopentyl (1) (17 g ) were added to a 250 mL Schlenk flask under $N_2$. The mixture was heated until the reaction took place (vigorous initiation as an exothermic reaction). The mixture was then cooled in an ice bath to prevent overheating. The mixture was heated to 100° C. for 6 hours. Ice water (300 mL) was added to this mixture and stirred at room temperature for 30 minutes. The mixture was extracted with pentane (3×20° C. mL) and the pentane extract was washed with 10% hydrochloric acid (3×20 mL), aqueous sodium bicarbonate (30 mL) and water (30 mL) and then dried over sodium sulfate. Removal of the pentane followed by distillation gave the product (55° C. at 1 mm) as a light yellow liquid. The yield was 81%.

The data for the 1,1'-dicyclopentyl (2) product were $^1H$ NMR (CDCl3): 5.6 (s, 4H), 2.52–2.41 (m), 1.96–1.83 (m) ppm.

From 1,1'-dicyclopentyl(2), the synthesis of BICP may proceed as follows:

(1R, 1'R)-Bicyclopentyl-(2S, 2'S)-diol was synthesized by asymmetric hydroboration of bi-1-cyclopenten-1-yl using (+)-monoisopinocampheylborane (sometimes referred to hereinafter as "(+)-$IpcBH_2$" or simply "$pcBH_2$") according to the procedure described in H. C. Brown, et al., *J. Org. Chem.* 1982, 47, 5074, incorporated by reference herein. It may be noted that a product having the opposite enantlomeric configuration would be produced using the (−)-$IpcBH_2$. The solution of enantiomerically pure (+)-$IpcBH_2$ (0.6 M, 200 mmol, 300 mL in ether) was cooled to −20° C. and HCl in ether (200 mL, 1.0 M, 200 mmol) was slowly added to this solution. The mixture was stirred for 30 min at 0° C. and then was cooled to −25° C. 1,1'-dicyclopentyl (10 g, 75 mmol) was added and the mixture was stirred at −25° C. for 24 hours. The mixture was warmed to 0° C. and stirred for another 24 hours. The reaction was quenched with methanol at −25° C. Hydroperoxide work-up was performed as described in the abovementioned H. C. Brown article. The crude mixture was purified by chromatography (first hexane/ethyl acetate (5/1) and then hexane/ethyl acetate (3/1)). The first component eluted is pinene alcohol, the second component is the desired diol (2.56 g, yield 18.3%, 93% enantiomeric excess) and the third component is meso diol (7.3 g, yield 58%). The absolute configuration of the diol was assigned based on the asymmetric hydroboration of trisubstituted olefins (e.g. methylcyclopentene) using (+)-$IpcBH_2$.

Data for the diol were as follows: $^1H$ NMR ($CDCl_3$, 300 MHz) 67 4.04(br, 2 H), 3.84 (m, 2 H), 2.02 (m, 2 H), 1.66–1.22 (m, 10 H), 1.21 (m, 2 H); $^{13}C$ NMR δ78.6 52.2 33.6, 29.2, 20.5; MS m/z 170 (M+, 0.35), 152, 134, 108, 95, 84, 68, HRMS calcd for C10111802: 170.1307(M+); found: 170.1315. Enantiomeric excess was determined by a chiral capillary GC column (Supelco TM γ-DEX 225, 160° C. t meso diol=19.88 min, (1R, 1'R, 2S, 2'S) diol=20.92 min, (1S, 1'S, 2R, 2'R) diol=21.42 min).

(1R,1'R)-Bicyclopentyl-(2S,2'S)-diol bis (methanesulfonate) was synthesized from the above diol. To a solution of (1R, 1'R)-bicyclopentyl-(2S, 2'S)-diol (0.8 g, 4.65 mmol) and triethylamine (1.68 mL, 12.09 mmol) in $CH_2Cl_2$ (30 mL), was added dropwise a solution of methanesulfonyl chloride (0.76 mL, 9.92 mmol) in $CH_2Cl_2$(2 mL) at 0° C. The reaction mixture was stirred at 0° C. for 30 min, and at room temperature for 2 h, then quenched by saturated aqueous ammonium chloride solution (25 mL). The aqueous layer was extracted with $CH_2Cl_2$ (3×20 mL) and the combined organic solution was dried over $Na_2SO_4$. After evaporation of the solvent, a white solid was obtained, which was used directly for the next step.

Data for the diol-methanesulfonate were $^1H$ NMR ($CDCl_3$, 200 MHz) δ5.01 (m, 2 H), 3.04 (s, 6 H), 2.17 (m, 2 H), 2.15–1.65 (m, 10 H), 1.43–1.52 (m. 2 H); δ86.8, 48.2, 38.4, 32.8, 27.4,22.5.

To synthesize (1R, 1'R, 2R, 2'R ) -1,1'-Bis (2-diphenylphosphino)cyclopentyl bisborane, diphenylphosphine (1.25 mL, 7.0 mmol) in THF (80 mQ) was cooled to −78° C. To this solution, n-BuLi in hexane (4.1 mL, 6.6 mmol) was added via syringe over 5 min. The resulting orange solution was warmed to room temperature and stirred for 30 min. After cooling the mixture to −78° C., the above (1R, 1'R, 2S, 2'S)1,1'-bicyclopentyl-2,2'-diol bis-mesylate (1.01 g, 3.1 mmol) in THF (20 mL was added over 20 min. The resulting orange solution was warmed to room temperature and stirred overnight. The white suspension solution was hydrolyzed with saturated aqueous $NH_4Cl$ solution. The aqueous layer was extracted with $CH_2$ $Cl_2$ (2×20 mL). The combined organic solution was dried over anhydrous $Na_2SO_4$. After removal of the solvents under reduced pressure, the residue was dissolved in $CH_2Cl_2$ (50 mL), then treated with $BH_3$-THF (10 mL, 10 mmol) at room temperature and the mixture was stirred overnight. The reaction mixture was added to $NH_4Cl$ aqueous solution, and extracted with $CH_2Cl_2$ (2×50 mL). The combined organic solution was dried over anhydrous $Na_2SO_4$. After evaporation of the solvent under reduced pressure, the residue was subjected to column chromatography on silica gel, eluting with $CH_2Cl_2$/hexane (1:5) and then $CH_2Cl_2$/hexane (2:3) affording the product as a white solid. Yield: 0.36 g (21%).

Data for the compound were: $^1H$-NMR ($CDCl_3$) δ7.80–7.30 (m, 20 H, Ph), 2.55–2.35 (m, 2 H, CHP($BH_3$) $Ph_2$), 1.95–1.35 (m, 14 H, $CH_2$ and CH), 1.7–0.5 (broad, 6 H, $BH_3$). $^{31}P$-NMR ($CDCl_3$): δP=17.5 (br). $^{13}C$-NMR ($CDCl_3$) δ133.43 (d, $^2J(PC)$=8.5 Hz, $C_{ortho}$), 132.08 (d,$^2J$ (PC)=8.5 Hz, $C_{ortho}$), 132.08 (d, $^1J(PH)$=50.0 Hz, $C_{ipso}$), 130.67 (d, $^4J(PC)$=2.1 Hz, $C_{para}$), 130.57 (d, $^4J(PC)$=2.1 Hz, $C_{para}$), 129.71 (d, $^1J(PC)$=56.5 Hz, $C_{ipso}$), 128.39 (d, $^3J(PC)$=9.4 Hz, $C_{meta}$), 128.29 (d, $^3J(PC)$=9.1 Hz, $C_{meta}$), 46.28 (dd, J(PC)=2.1 and 4.8 Hz, C 1,1,), 36.26 (d, $^1J(PC)$= 30.6 Hz, $C_{2,2}$), 31.19 ($CH_2$), 29.52 ($CH_2$), 22.51 ($CH_2$); MS m/z 520 (8.95), 506 (3.55), 429(19.10), 321(100), 2.53 (7.45), 185(26.64), 108(43.68), 91(11.99), 77(6.88), HRMS cacld for $C_{28}H_{31}$ $P_2$ (M+−$B_2H_6$−Ph): 429.1901, found: 429.1906.

(2R, 2'R)-Bis(diphenylphosphino)-(1R, 1'R)-dicyclopentane (sometimes referred to hereinafter as "(R,R) BICP", or simply "BICP") was synthesized by adding tetrafluoroboric acid-dimethyl ether complex (0.55 mL, 4.5 mmol) dropwise via syringe at −5° C. to a solution of the above borane complex of the phosphine (0.24 g, 0.45 mmol) in $CH_2Cl_2$ (4.5 mL). After the addition, the reaction mixture was allowed to warm slowly to room temperature, and stirred for 20 hours. The mixture was diluted with $CH_2Cl_2$, and neutralized with saturated aqueous $NaHCO_3$ solution. The aqueous layer was extracted with $CH_2Cl_2$. The combined organic solution was washed with brine, followed by water, and dried over $Na_2SO_4$. Evaporation of the solvent gave the pure phosphine. Yield: 0.21 g (93%).

Data for the compound were: $^1$H NMR (CDCl$_3$, 360 MHz) δ7.52–7.27 (m, 20 H), 2.53 (m, 2 H), 2.27 (m, 2 H), 1.93(m, 2 H), 1.72(m, 2 H), 1.70–1.43 (m, 8 H); 13C NMR (CDCl$_3$) δ139–127 (Ph), 45.9 (d, J=12.1 Hz), 45.8 (d, J=12.0 Hz), 40.34 (d, J=14.0 Hz), 30.9 (m), 23.8 (m); $^{31}$p NMR (CDCl$^3$) δ–14.6. This phosphine was fully characterized by its borane complex.

The above example is non-limiting, and other synthetic routes for obtaining BICP are described in co-pending application Ser. No. 08/876,120.

Synthesis of (2S, 2'S)-bis(diphenylphosphinoxy)-(1R, 1'R)-dicyclopentane (1R, 1'R)-Bicyopentyl-(2S, 2'S)-diol was made according to methods set forth in G. Zhu, et al., "Highly Enantioselective Rh-catalyzed Hydrogenations with a New Chiral 1, 4-Diphosphine Containing a Cyclic Backbon," *J. Am. Chem. Soc.* 119(7), 1799–1800 (1977), incorporated by reference herein.

(2S, 2'S)-Bis(diphenylphosphinoxy)-(1R, 1'R)-dicyclopentane $^1$H-NMR (CDCl$_3$) δ7.50~7.43 (m, 8 H), 7.36~7.26 (m, 12 H), 4.22~4.20 (m. 2 H), 2.15 (m. 2 H). 182~1.66 (m, 8 H), 1.59~1.53 (m. 2 H), 1.28~1.21 (m. 2H); $^{31}$P-NMR (CDCl$_3$): δP=106.7; $^{13}$CNM-R (CDCl$^3$) δ143.18–142.70 (m), 130.38–130.07 (m), 128.90 (s. 129.18–128.08 (m), 85.56 (d, J=17.9 Hz), 49.29 (d, J=6.52 Hz), 33.78 (d, J=5.61 Hz). 27.06 (s). 22.59 (s). MS m/z: 538, 461, 383, 353, 337, 201, 185, 151, 135, 77; HRMS calcd for C$_{34}$H$_{36}$O$_2$P$_2$ (M+): 538.2190. found: 538.2156.

(1R, 1'R)-Bicyclopentyl-(2R, 2'R)-diol $[α]^{25}_D$=–54.0 (c, 1.07 CHCl$_3$): $^1$H-NMR (CDCl$_3$) δ4.30~4.28 (m, 2H), 1.87~1.49 (m, 14 H); $^{13}$C-NMR (CDCl$_3$) δ74.21. 45.59 35.23. 28.27. 21.62. MS m/z: 152, 134, 121, 108, 67, 41, 37; HRMS calcd for C$_{10}$H$_{17}$O (M+–OH): 153.1279; found: 153.1238.

(2R, 2'R)-Bis(diphenylphosphinoxy)-(1R, 1'R)-dicyclopentane $^1$H-NMR (CDCl$_3$) δ7.48~7.40 (m. 8 H), 7.35~7.27 (m, 12 H), 4.11~4.09 (m. 2 H), 1.86~1.70 (m. 8 H). 1.58~1.50 (m, 4 H), 1.50~1.30 (m, 2H), $^{31}$P-NMR (CDCl$_3$): δP=106.1; $^{13}$C-NMR (CDCl$_3$) δ143.79~142.70 (m), 131.19~127.99 (m), 83.44 (dd, J$_1$=2.01 Hz, J2=19.4 Hz). 46.03 (d. J=6.44 Hz), 33.42 (d, J=4.98 Hz), 28.30 (s), 21.58 (s). MS m/z: 538, 461, 383, 353, 337, 269, 201, 185, 151, 135, 77; HRMS calcd for C$_{34}$H$_{36}$O$_2$P$_2$) (M+): 538.2190. found: 538.2159.

Determination of Enantiomeric Excess

Chiral Capillary GC. Column: Chirasil-VAL III FSOT column. Dimensions: 25 m×0.25 mm (i.d.). Carrier gas: He (1 mL/min). The racemic products were obtained by hydrogenation of substrates with an achiral catalyst. The following is the retention time for the racemic products: N-Acetylphenylalanine methyl ester (capillary GC, 150° C., isothermal) (R) t$_1$=14.66min. (S) t$_2$=16.23 min, N-acetylaianine methyl ester (capillary GC, 100° C., isothermal) (R) t$_1$=5.56 min, (S) t$_2$=6.73 min; N-acetyl-m-bromophenylalanine methyl ester (capillary GC, 180° C., isothermal) (R) t$_1$=14.14 min, (S) t$_2$=15.09 min. N-benzoylphenylalanine methyl ester (capillary GC, 180° C., isothermal) (R) t$_1$=35.65 min, (S) t$_2$=37.13 min: N-Acetylleucine methyl ester (capillary GC, 110 ° C., isothermal) (R) t$_1$=16.1 min. (S) t$_2$=19.4min. N-Acetyl-p-fluorophenylalanine methyl ester (capillary GC. 180° C. isothermal) (R) t$_1$=5.02 min, (S) t$_2$=5.28 min; N-Acetyl-o-chlorophenylalanine methyl ester (capillary GC, 180° C., isothermal) (R) t$_1$=9.32 min, (S) t$_2$=–9.78 min: N-Acetyl-3 (2-naphthyl)alanine methyl ester (capillary GC, 190° C., isothermal): (R) t$_1$=27.88 min. (S) t$_2$, =29.30 min; N-Acetyl-3-(2-thienyl)alanine methyl ester (capillary GC. 170° C. isothermal) (R) t$_1$=7.21 min, (S) t$_2$=7.54 min.

Chiral HPLC. Column: Daicel Chiralcel OJ (p-toloyl cellulose ester coated on silica gel). Particle size: 5.0 um. Column dimensions: 25 cm (length)×0.46 cm (i.d.). Colulmn temperature: 25° C. N-Acetyl-p-methoxyphenylalanine methyl ester (HPLC, 1.0 mL/min, 10% 2-PrOH/hexane), (S) t$_1$=62.52 min, (R) t$_2$=72.45 min, N-Acetyl-p-acetoxy-m-methoxyphenylalanine methyl ester (HPLC, 1.0 mL/min, 10% 2-PrOH/hexane). (R) t$_2$=70.75 min, (S) t$_1$=73.70 min.

Synthesis of Modified BICP

To a mixture of Mg (6.70 g, 0.275 mmol) in THF (150 mL) was added a solution of 3.5-dimethylphenylbromide (50 g, 0.262 mmol) in THF (50 mL) dropwise. After addition, the mixture was cooled to room temperature, and then stirred for another hour. The reaction mixture was cooled to 0° C., a solution of PCl$_3$ (5.08 mL, 58 mmol) in THF (10 mL) was added slowly. Then the reaction mixture was heated at reflux for 2 hours. The reaction mixture was quenched with NH$_4$Cl (sat. aq. at 0° C.). Extracted by benzene, the combined organic layer was washed by NaHCO$_3$, and brine. After drying over sodium sulfate, the solvent was removed under reduced pressure. The product was obtained by recrystallization from EtOH, 10.5 g.

To a solution of triaryl phosphine (28.0 g. 80.8 mmol) in THF (210 mL) was added Li (1.17 g, 2.08 eq) in portions. Then the reaction was stirred at room temperature for two days. The reaction was quenched by adding water at 0° C., and stirred until all solid was dissolved. Extracted with ether (3×40 mL), the combined organic layer was washed with HCl (1~2% aq., followed by water (40 mL×3). Dried over Na$_2$SO$_4$, after the solvent was evaporated, the product was obtained by distillation: 16.0 g, 160~165° C./0.2 mmHg.

To a solution of (1R, 1'R-bicyclopentyl-(2S, 2'S)-diol (1 g, 5.87 mmol) and triethylamine (2.13 mL) in CH$_2$Cl$_2$ (40 mL) was added dropwise a solution of methanesulfonyl chloride (0.973 mL) in CH$_2$Cl$_2$ (2 mL) at 0° C. After 30 min at 0° C., the reaction mixture was stirred for additional 2h at room temperature, then quenched by saturated aqueous ammonium chloride solution (25 mL). The aqueous layer was extracted with CH$_2$Cl$_2$ (3×20 mL) and the combined organic solution was dried over Na$_2$SO$_4$. After evaporation of the solvent, a white solid was obtained, (1R, 1'R)-Bicyclopentyl-(2S, 2'S)-diol bis (methanesulfonate), which was used directly for the next step.

Data for the compound were as follows: $^1$H NMR (CDCl$_3$, 200 MHz) δ5.01 (m, 2H), 3.04 (s, 6 H), 2.17 (m, 2H), 2.15–1.65 (m, 10 H), 1.43–1.52 (m, 2 H); $^{13}$CNMR δ86.8, 48.2, 38.4, 32.8, 27.4, 22.5.

To a solution of diarylphosphine (3.19 g) in THF (140 mL) was added n-BuLi in hexane (7.7 mL, 1.6 M) at –78°

C. over 5 min via syringe. The resulting orange solution was warmed to room temperature and stirred for 30 min. After cooling the mixture to −78° C., (1R, 1'R, 2S, 2'S)-1,1'-bicyclopentyl-2,2'-diol bismesylate in THF (20 mL) was added over 30 min. The resulting orange solution was warmed to room temperature and stirred overnight. The white suspension solution was hydrolyzed with saturated aqueous $NH_4Cl$ solution. The aqueous layer was extracted with $CH_2Cl_2$ (3×20 mL), and the combined organic solution was dried over anhydrous $Na_2SO_4$. After removal of the solvents under reduced pressure, the residue was dissolved in $CH_2Cl_2$ (90 mL), then treated with $BH_3$. THF (19 mL) at room temperature and the mixture was stirred overnight. The reaction mixture was added to $NH_4Cl$ aqueous solution, and extracted with $CH_2Cl_2$ (3×50 mL). The combined organic solution was dried over anhydrous $Na_2SO_4$. After evaporation of the solvent under reduced pressure, the residue was subjected to column chromatography on silica gel. The product was the desired (1 R, 1'R, 2R, 2'R)-1,1'Bis(2-diarylphosphino)cyclopentyl bisborane, formed with a yield of 1.0 g.

Data for the compound were as follows: $[\alpha]^{25}_D = -9.63$ (c 1.36, $CHCl_3$); 1H NMR ($CDCl_3$, 300 MHz) δ7.25~7.21 (m, 4H), 7.07 (s, 2H), 7.00~6.98 (m, 4H), 6.94 (s, 2H), 2.40 (s, 12H), 2.34 (s, 12 H), 2.33~2.19 (m, 2H), 1.83~1.29 (m, 14 H); $^{13}C$ NMR ($CDCl_3$) δ139.9~125.2 (Ph), 47.6~47.1 (m), 39.1 (d, 14.0 Hz), 30.9(m), 22.4(m), 21.4, 21.3; $^{31}P$ NMR ($CDCl_3$) δ−16.9.

(2R, 2'R)-Bis(diarylphosphino)-(1R, 1'R)-dicyclopentane was made as follows: To a solution of the above borane complex of the phosphine (0.95 g mmol) in $CH_2Cl_2$ (14.6 mL) was added tetrafluoroboric acid-dimethyl ether complex (1.79 mL) dropwise via syringe at −5° C. After the addition, the reaction mixture was allowed to warm slowly to room temperature, and stirred for 20 hours. The mixture was diluted with $CH_2Cl_2$, and neutralized with saturated aqueous $NaHCO_3$ solution. The aqueous layer was extracted with $CH_2Cl_2$. The combined organic solution was washed with brine, followed by water, and dried over $Na_2SO_4$. Evaporation of the solvent gave the pure phosphine.

Synthesis of PennPhos

The synthesis of PennPhos and many derivatives is described in co-pending application 08/876,120. Referring to Scheme 2, additional details of the synthesis are set forth below.

To synthesize 1,4-Dimethylcyclohexane-1,4-diene, 250 ml ethylamine was charged to a 1 L flask fitted with cooling finger (−78° C.) and a stirring bar, and the solution was cooled to 0° C. Then, anhydrous p-xylene (54.9g, 64 ml, 517 mmol) was added followed by the addition of ethyl alcohol (3×60 ml). Lithium wires (5.6 g) were added after each portion of ethyl alcohol (in total 16.8 g Lithium was added). After 3 h, the mixture was quenched with ice water (heat evolved). The aqueous layer was extracted with ether (3×150 ml), then dried over anhydrous sodium sulfate. The solvent was removed by rotary evaporation. The residue was distilled and the product (30 g, 53.7%) was collected at 135–140° C.

(1S,2R,4S,5R)-(+)-2,5-Dimethylcyclohexane-1,4-diol was synthesized as follows. A 500 ml flask fitted with a rubber septum and a magnetic stirring bar was charged with $IpcBH_2$ (assumed 0.6 M, 300 ml, 18 1 mmol) in ether and cooled to −25° C. The $IpcBH_2$ was derived from (1 R)-(+)-α-pinene, 98%, 92+% enantiomeric excess, obtained from the Aldrich Chemical Co.; as with the previous example, the chirality of the product can be reversed using the (1 S)-(−)-α-pinene. 1,4-Dimethylcyclohexane-1,4-diene (7.5 g, 69.3 mmol) was added via syringe over 4 min. The reactants were stirred for 24 h at −25° C. and for 24 h at 0° C. The mixture was quenched with methanol (12.8 ml, 316 mmol) dropwise at −25° C. (hydrogen evolved). The solution was transferred to a 2 L flask and cooled to 0° C., then oxidized by successive slow addition of sodium hydroxide (4 M, 119 ml, 475 mmol) and hydrogen peroxide (30%, 49 mL, 475 mmol). The mixture was maintained at room temperature overnight. Two layers separated. The aqueous layer was extracted with ether (3×150 mL). The combined organic portion was dried over anhydrous sodium sulfate, and the solvent was removed under vacuum. The oily residue was subjected to flash chromatography (Silica gel, 5:1 methylene chloride/acetone) and gave first pinene alcohol, $C_1$-symmetrical diol and then desired $C_2$-symmetrical diol as a white solid (5.5 g, 55%, 96% enantiomeric excess by GC using a Supleco β-120 column).

(1S, 2R, 4S, 5R)-Dimethylcyclohexane-1,4-dimesylate was synthesized as follows. To a solution of (1S, 2R, 4S, 5R)-Dimethylcyclohexane-1,4-diol (16 g, 111 mmol) and triethylamine (37.6 mL, 267 mmol) in dry methylene chloride (500 mL) was added dropwise the solution of methanesulfonyl chloride (17.3 mL. 221.3) in methylenie chloride (30 mL) at 0° C. The mixture was stirred for 30 min at 0° C. and for 2.5 h at room temperature. The reaction was quenched with saturated ammonium chloride solution (200 mL) at. 0° C. The aqueous layer was extracted with methylene chloride (3×150 mL). The combined organic phase was dried over anhydrous sodium sulfate and concentrated under vacuum, giving a light yellow solid. This product was passed through a short column of silica gel eluted with methylene chloride, which gave the desired product as a white solid (33.3 g, 99.9%).

To make (1R, 2S, 4R, 5S)-(+)-2,5-Dimethyl-7-phenyl-7-phosphabicyclo[2.2.1]heptane borane (FIG. 2, (5)), n-BuLi (34.5 mL of a 1.6 M solution in -hexane, 55 mmol) was added via syringe at −78° C. over 20 min to phenylphosphine (3.0 ml, 27.3 mmol) in THF (200 mL). Then the orange solution was warmed up to room temperature and stirred for 1 hr at room temperature. To the. resulting orange-yellow suspension was added a solution of (1S,2S,4S,5S)-2,5-dimethycyclohexane- 1,4-diol bis (methanesulfonate) (8.25 g, 27.5 mmol) in THF (100 mL) over 15 min. After the mixture was stirred overnight at room temperature, the pale-yellow suspension was hydrolyzed with saturated $NH_4Cl$ solution. The mixture was extracted with ether (2×50 mL), and the combined organic solution was dried over anhydrous sodium sulfate. After filtration, the solvents were removed under reduced pressure. The residue was dissolved in methylene chloride (100 mL), treated with $BH_3$-THF (40 mL of a 1.0 M solution in THF, 40 mmol) and the mixture was stirred overnight. It was then pured into saturated $NH_4Cl$ solution and extracted with $CH_2C_2$ (3×50 mL). The combined organic solution was dried over anhydrous $Na_2SO_4$ and filtered, the solvent was removed on reduced pressure. The residue was subjected to chromatography on slicon gel column, eluted with hexanes/$CH_2Cl_2$ (4:1) affording the product as a white solid. Yield: 1.95 g (31%).

Data for the compound were as follows: $[\alpha]^{25}D = +59.5°$ (c 1.07, $CHCl_3$). $^1H$-NMR ($CDCl_3$) δ7.60–7.30 (m, 5 H, $C_6\underline{H}_5$), 2.60–2.40 (m, 2 H. C$\underline{H}P(BH_3)Ph$), 2.15–2.05 (m. 1 H C$\underline{H}$), 2.04–1.80 (m, 4 H, C$\underline{H}_2$), 1.65–1.50 (m, 1 H, C$\underline{H}$), 1.32 (d, $^3J(HH)=6.5$ Hz 3 H, C$\underline{H}$-3), 0.59 (d, $^3J(HH)=6.7$ Hz, 3 H, C$\underline{H}_3$), 1.6–0.2 (br, B$\underline{H}_3$)-$^{13}$C-NMR ($CDCl^3$) δ131.74 (d, $^2J(PC)=7.3$ Hz, $Ch_{ortho}$), 130.56 (d, $_1J(PC)=43.9$ Hz, $C_{ipso}$), 129.92 (d, $^4$J(PC) =2.0 Hz, C$_{para}$), 128.44 (d, $^3$J(PC)=8.6 Hz, C$_{meta}$), 43.07 (d, $^1$J (PC)=30.5 Hz, CHP(BH$_3$)Ph), 40.85 (d, $^1$J(PC)=31.6 Hz,.CHP(BH3)Ph), 36.27 (CH$_2$), 36.67 (d, $^3$J(PC) 13.5 Hz, CH$_2$), 35.91 (d, $^2$J(PC)=3.5 Hz, CH), 34.65 (d, $^2$J(PC)=9.8 Hz, CH), 20.78 (CH3) 20.53 (CH3); $^{31}$P-NMR (CDCl$^3$) δ36.3 (d, broad, $^1$J(PB)=58.8 Hz); HRMS Calcd for C$_{14}$H$_{22}$BP: 232.1552 (M+); found: 232.1578; C$_{14}$H$_{19}$P: 218–1224 (M$^+$-BH3); found: 218.1233.

(1R, 2R, 4R, 5R)-(+)-2,5-Diisopropyl-7-phenyl-7-phosphabicyclo[2.2.1]heptane borane (FIG. 2, (6)) was synthesized using the same procedure as in the preparation of (5), with a yield of 50%.

The product was characterized as follows: [α]25 D=+25.5° (c 1.02, CHCl$_3$)-1 H-NMR (CDCl$_3$) δ7.55–7.30 (m, 5 H, C$_6$H$_5$), 2.85–2.70 9 (m, 2 H $_{CH}$P(BH$_3$)Ph), 2.30–2.20 (m, I H, CH), 2.18–2.00 (m, 1 H, CH), 1.95–1.65 (m, 4 H, CH$_2$), 1.40–1.20 (m, 2 H, CH), 1.03 (d, $^3$J(PH)=6.5 Hz, CH$_3$), 0.87(d, $^3$J(PH)=6.7 Hz, CH$_3$), 0.85 (d, $^3$J(PH)=7.4 Hz, CH$_3$), 0.53 (s, broad, 3 H, CH$_3$), 1.5–0.2 (broad, BH$_3$); $^{13}$C-NMR (CDCl$_3$) δ131.19 (d, $^2$J(PC)=8.3 Hz, C$_{ortho}$), 130.71 (d, $^1$J(PC)=45.2 Hz, C$_{ipso}$) 129.97 (d, $^4$J(PC)=2.5 Hz, C$_{para}$), 128.45 (d, $^3$J(PC)=9.5 Hz, C$_{meta}$), 50.30 (d, $^2$J(PC)= 2.1 Hz, CH), 48.77 (d, $^2$J(PC) 9.7 Hz, CH), 38.27 (d, $^1$J(PC)=30.5 Hz, CHP(BH$_3$)Ph), 36.81 (CH$_2$) 36.71 (d, $^1$J(PC)=31.5 Hz, CHP(BH$_3$) Ph), 34.73 (d, $^3$J(PC)=13.7 Hz, CH$_2$), 31.9:2 (CHMe$_2$ ). 31.12 (CHMe2), 22.41 (CH$_3$), 21.55 (CH$_3$), 20.73 (CH$_3$), 20. 10 (CH$_3$); $^{31}$P-NMR (CDCl$_3$) δ36.d (d, broad, $^1$J(PB)=51.4 Hz).

(1R, 2S, 4R, 5S)-(+)-2,5-Dimethyl-7-phenyl-7-phosphabicyclo[2.2.1] heptane (7) To a solution of corresponding borane complex of the phosphine (5, 1.0 g, 4.31 mmol) in CH$_2$Cl$_2$ (22 mL) was added tetrafluoroboric acid-dimethyl ether complex (2.63 mL, 21.6 mmol) dropwise via a syringe at −5° C. After the addition, the reaction mixture was allowed to warm up slowly, and stirred at room temperature. After 20 h, $^{31}$P NMR showed the reaction was over, it was diluted by CH$_2$Cl$_2$, neutralized by saturated NaHCO$_3$ aqueous solution. The aqueous layer was extracted with CH$_2$Cl$_2$. The combined organic solution was washed with brine, followed by water, and then dried over Na$_2$SO$_4$. Evaporation of the solvent gave a pure phosphine product, which was confirmed by NMR. Yield: 0.9 g (96%).

Data for the compound were as follows. [α]$^{25}$D=+92.5° (c 2.3, toluene); $^1$H NMR (CDCl$_3$, 360 MHz) δ7.38–7.34 (m, 2H), 7.26–7.21 (m, 2H), 7.19–7.16 (m, 1H), 2.60–2.54 (m, 2H), 1.89–1.62 (m, 5H), 1.44–1.42 (m, 1H), 1.16 (d, J=6.12 Hz, 3 H), 0.55 (d, J=6.95 Hz, 3H); $^{13}$C NMR (CDCl$_3$) δ138.68 (d, J=29.3 Hz), 131.42 (d, J=13.0 Hz), 127.88 (d, J=2.35 Hz), 126.57 (s), 47.34 (d, J=13.5 Hz), 45.26 (d, J=10.2 Hz,') 39.21 (d, J=6.7 Hz), 39.21 (d. J=5.3 Hz), 38.74 (d, J=6.7 Hz), 34.69 (d. 17.2 Hz), 22.37 (d, J=7.8 Hz), 21.52 (S); $^{31}$ p NMR(CDCl$_3$) δ-7.29.

Me-PennPhos: 1,2-Bis((1R,2S,4R,5S)-2,5-dimethyl-8-phenylphospha -bicyclo[2.2.1]heptyl)benzene. To the suspension of NaH (8.0 g, 333 mmol) in THF (200 ml), cooled to 0° C., was added 1,2-diphosphinobenzene (4.0 ml, 30.4 mmol), followed by HMPA (80 ml). The resulting orange suspension was stirred at 0° C for 1 hours. (1S,2S,4S,5S)-2,5-dimethylcyclohexane-1,4-diol dimesolate (18.3 g, 60.9 mmol) in THF (150 ml) was added over 20 min. The resulting orange-red suspension was stirred at room temperature for 3.5 days, hydrolyzed with NaCl-H$_2$O and then extracted with hexane (2×100 ml). The combined organic solution was dried over Na$_2$SO$_4$. After filtration, the solvents were removed under reduced pressure. The residue was subjected to chromatography on silica gel column, eluted with hexane. Yield: 3.0 g (27.5%).

Data for the compound were as follows: $^1$H-NMR (CDCl$_3$): δH=7.25–7.10 (IM, 2 H, aromatic), 7.08–6.95 (m, 2 H, aromatic), 3.21 (d, broad, 2 H. $^2$J(PH)=14.5 Hz, PCH), 2.58 (d, broad, 2 H, $^2$J(PH)=13.4 Hz, PCH), 1.90–1.60 (m, 12 H), 1.55–1.35 (m, 2 H,) 1.17 (d, 6 H, $^3$J(HH)=6.3 Hz, CH$_3$). 0.60 (d, 6 H, $^3$J(HH)=6.3 Hz, CH$_3$). CH. $^{13}$C-NMR (is out of first order, CDCl$_3$): δC=143.94, 143.66, 143.48, 143.20, 131.05, 131.00, 130.93, 126.33, 46,24, 46.20, 46,17, 46.13,45.92, 45.69, 45.61, 45.38, 40.17, 40.05, 39.89, 39.73, 39.61, 39.52, 39.33, 39.29, 39.26, 34.76, 34.61. 34.51, 34.41, 34.26, 22.69, 22.65, 22.61, 20.82. $^{31}$P-NMR (CDCl$_3$): δP=−7.3 ppm.

i-Pr-PennPhos: 1,2-Bis{(1R,2R,4R,5R)-2,5-bis-isopropyl-8-phenylphos-phabicyclo[2.2.1] heptyl} benzene. 1,2-diphosphinobenzene (0.4 ml, 3.04 mmol) and NaH (0.9 g, 37.5 mmol) were mixed in THF (50 ml) and cooled to 0° C. HMPA (8.5 ml, 49 mmol) was added. The resulting orange suspension was stirred at 0° C. for 1 h and then (1S,2S,4S,5S)-2,5-dimethyl-cyclohexane-1,4-diol dimesolate (2.17 g, 6.08 mmol) in. THF (40 ml) was added over 10 min. The resulting orange-red suspension was stirred at room temperature for 3 days. After cooled to 0° C., it was hydrolyzed with NaCl—H$_2$O,and extracted with hexane (2×50 ml). The combined organic solution was dried over Na$_2$SO$_4$ and filtered. The solvents were removed under reduced pressure. The residue was subjected to chromatography on silica gel column, eluted with hexane. Yield: 0.6 g (42%).

Data for the compound were as follows: $^1$H-NMR (CDCl$_3$): δH=7.20–7.10 (m, 2 H, aromatic), 7.05–6.90 (m, 2 H, aromatic), 3.38 (d, broad, 2 H, $^2$J(pH)=14.2 Hz, PCH), 2.85 (d, broad, 2 H, $^2$J(PH)=13.5 Hz, PCH), 1.85–1.45 (m, 12 H), 1.30–1.08 (m, 4 H), 1.03 (d, 6H, $^3$J(HH)=6.4 Hz, CH3), 0.96 (d, 6H, $^3$J(HH)=5.6 Hz, CH3), 0.86 (d, 6H, $^3$J(HH)=6.5 Hz, CH$_3$), 0.47 (s, 6 H, CH$_3$). $^{13}$C-NMR (is out of first order, CDCl$_3$): δC=143.97, 143.62, 143.56, 143.50, 143.45, 143.09, 130.96, 130.90,130.86, 126.11, 54.10, 54.06, 54.03,48.65, 48.56,48.46.42.02, 41.96, 41.24,41.20, 41.18, 41.14, 37.94, 37.77, 37.60, 37.46, 33.29, 33.27, 33.24, 31.69, 23,45, 23.40, 23.35, 22.22. 20.97, 20.54. $^{31}$P-NMR (CDCl$_3$): δP=−8.7 ppm.

Synthesis of BICPO

Data for the phosphinite compound is as follows: $^1$H-NMR (CDCl$_3$) δ7.50~7.43 (m, 8 H), 7.36–7.26 (m, 12 H), 4.22~4.20 (m. 2 H). 2.15 (m, 2 H), 1.82~1.66 ( m,8 H), 1.59~1.53 (m, 2 H), 1.28~1.21 (m. 2H); $^{31}$P-NmR (CDCL$_3$): δP=106.7; $^{13}$C-NMR (CDCL$_3$) δ143.18~142.70 (m), 130.38~130.07 (m). 128.90 (s), 128.18~128.08 (m), 85.56 (d, J=17.9 Hz), 49.29 (d. J=6.52 Hz), 33.78 (d. J=5.61 Hz). 27.06 (s). 22.59 (s). MS m/z: 538, 461, 383, 353, 337. 201.185.151. 135. 77: HRMS calcd for C$_{34}$H$_{36}$O$_2$P$_2$)(M+): 538.2190; found: 538.2156.

The enantiomer, (1R, 1'R, 2R, 2'R)-BICPO may be made by converting the absolute configurations of the 2,2' positions of the (1R,1 'R)-bicyclopentyl-(2S, 2'S)-diol into (1R, 1'R)-bicyclopentyl-(2R, 2'R)-diol via a Mitsunobu reaction. This process is completely described by M. J. Arco, et al.," J. Org. Chem. 1976. 41. 2075 and D. L. Hughes, L. Org. React. 1992, 42 387, which are incorporated by reference herein. Thus, a new bisphosphinite chiral ligand (1R, 1'R, 2R, 2'R) BICPO, having the same configuration as the original (1R, 1'R. 2R, 2'R)-BICP was made according to the above reaction scheme, but with a yield of 74.4%.

Other methods may be used to obtain the chiral product with the desired enantiomeric configuration, as described herein in connection with the BICP and in co-pending parent application 08/876,120. The reaction conditions and reagents employed are exemplary only, and are not intended to be limiting of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A chiral bisphosphine ligand for performing asymmetric synthesis, wherein said ligand comprises an enantiomer of a (2, 2')-bis(diarylphosphino)-(1,1')-dicyclo compound having saturated carbons at the 2, 2', 1, and 1' positions, and wherein each aryl is 3, 5-alkyl substituted or 4-alkyl substituted.

2. The chiral ligand of claim 1, wherein said aryl is 3, 5-alkyl substituted.

3. The chiral ligand of claim 2, wherein said ligand comprises an enantiomer of (2, 2')-bis(3, 5-dimethylphenylphosphino)-(1,1')-dicycloalkane.

4. The chiral ligand of claim 2, wherein said ligand comprises an enantiomer of (2, 2')-bis(3, 5di-tert-butylphenylphosphino)-(1,1')-dicycloalkane.

5. The chiral ligand of claim 3, wherein said ligand comprises an enantiomer of (2, 2')bis(3, 5-dimethylphenylphosphino)-(1,1')-dicyclopentane.

6. The chiral ligand of claim 4, wherein said ligand comprises an enantiomer of (2, 2')-bis(3, 5di-tert-butylphenylphosphino)-(1,1')dicyclopentane.

7. The chiral ligand of claim 1, wherein said ligand comprises an enantiomer of (2, 2')-bis(4-methyl phenylphosphino)-(1,1')dicyclopentane.

8. The chiral ligand of claim 1, wherein said ligand comprises an enantiomer of (2,–2')-bis(4-tert-butyl phenylphosphino)-( 1,1')-dicyclopentane.

* * * * *

UNITED STATES PATENT AND TRADEMARK OFFICE
CERTIFICATE OF CORRECTION

PATENT NO. : 6,278,024 B1
DATED : August 21, 2001
INVENTOR(S) : Xumu Zhang

It is certified that error appears in the above-identified patent and that said Letters Patent is hereby corrected as shown below:

<u>Title page,</u>
Item [57], ABSTRACT,
Line 7, after "rigidity", insert a period, -- . --.

<u>Column 22, claim 4,</u>
Line 5, "5di-tert-" should read -- 5-di-tert- --.

<u>Column 22, claim 5,</u>
Line 8, "(2,2')bis(3," should read -- (2,2')-bis(3, --.

<u>Column 22, claim 6,</u>
Line 11, "5di-tert-" should read -- 5-di-tert- --.

Signed and Sealed this

Twenty-sixth Day of February, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,278,024 B1  
APPLICATION NO. : 09/524787  
DATED : August 21, 2001  
INVENTOR(S) : Xumu Zhang Page 1 of 1

It is certified that error appears in the above-identified patent and that said Letters Patent is hereby corrected as shown below:

Column 1, Line 15, after "CROSS REFERENCE TO RELATED APPLICATIONS" and before "BACKGROUND OF THE INVENTION" insert the following:

--GOVERNMENT SPONSORSHIP

This invention was made with Government support under Contract No. N00014-96-1-0733, awarded by the Office of Naval Research. The Government has certain rights in the invention.--

Signed and Sealed this

Twenty-first Day of April, 2009

JOHN DOLL  
*Acting Director of the United States Patent and Trademark Office*